(12) United States Patent
Catania et al.

(10) Patent No.: US 7,244,710 B2
(45) Date of Patent: Jul. 17, 2007

(54) TREATMENT OF OPHTHALMIC INFECTIONS USING ANTIMICROBIAL PEPTIDES

(75) Inventors: Anna P. Catania, Milan (IT); James M. Lipton, Woodland Hills, CA (US)

(73) Assignee: Zengen, Inc., Calabasas, CA (US)

(*) Notice: Subject to any disclaimer, the term of this patent is extended or adjusted under 35 U.S.C. 154(b) by 619 days.

(21) Appl. No.: 10/442,683

(22) Filed: May 21, 2003

(65) Prior Publication Data
US 2004/0033955 A1    Feb. 19, 2004

Related U.S. Application Data

(60) Provisional application No. 60/382,887, filed on May 21, 2002.

(51) Int. Cl.
A61K 38/00 (2006.01)
(52) U.S. Cl. .............................. 514/14; 514/18; 514/16; 514/2
(58) Field of Classification Search .................... None
See application file for complete search history.

(56) References Cited

U.S. PATENT DOCUMENTS

| 5,028,592 A | 7/1991 | Lipton |
| 5,891,847 A | 4/1999 | Naveh |
| 2002/0146374 A1 | 10/2002 | Lipton |

FOREIGN PATENT DOCUMENTS

| EP | 0 234 855 | 9/1987 |
| WO | WO 93/01211 | 1/1993 |

OTHER PUBLICATIONS

Dalai et al., Journal of NeuroVirology, vol. 8, pp. 35-44, 2002.*
Merchant et al., Cornea, vol. 20, No. 2, pp. 226-229, 2001.*
Hulem et al., Arch Ophthalmol. vol. 200, pp. 646-649, 1982.*
U.S. Appl. No. 09/957,765, filed Sep. 21, 2001, Anna P. Catania et al.
U.S. Appl. No. 09/535.066, filed Mar. 23, 2000, James M. Lipton et al.
U.S. Appl. No. 10/420,578, filed Apr. 21, 2003, James M. Lipton et al.
U.S. Appl. No. 10/426,647, filed Apr. 29, 2003, James M. Lipton et al.
U.S. Appl. No. 10/298,142, filed Nov. 15, 2002, James M. Lipton.
Aylad et al., Influence of Oral Acyclovir on Ocular Complications of Herpes zoster ophthalmicus, *Eye* 8: 70-74 (1994).
Armstrong, The Microbiology of the Eye, *Ophthal. Physiol. Opt.* 20: 429-503 (2000).
Deeter, L.B. et al., *Antipyretic Properties of Centrally Administered α-MSH Fragments in the Rabbit*, Peptides 9, 1285-8 (1989).
Doughtery et al., The Role of Tetracycline in Chronic Blepharitis: Inhibition of Lipase Production in *Staphylococcus*, *Inv. Ophthalmol. Vic. Sci.* 32: 2970-2975 (1991).
Hart, D.A. et al., *Staphylococcus aureus* Strains Differ in Their in Vitro Responsiveness to Human Urokinase: Evidence that Methicillin-Resistant Strains are Predominantly Nonresponsive to the Growth-Enhancing Effects of Urokinase, *Can. J. Microbiol.* 42, 1024-31 (1966).
Hiltz, M.E. et al., Anti-inflammatory Activity of α-MSH (11-13) Analogs: Influences of Alterations in Stereochemistry, *Peptides* 12, 767-71 (1991).
Holdeman, M. et al., Antipyretic Activity of a Potent α-MSH Analog, *Peptides* 6, 273-5 (1985).
Huberspitz et al., Corneal Ulceration: An Update from a Specialized Ambulatory Care Centre, *Klinische. Monals. Augen.* 200: 251-256 (1992).
Ishibashi & Kaufman, The Effects of Subconjunctival Miconozole in the Treatment of Experimental *Candida* Keratitis in Rabbits, *Arch. Ophthalmol.* 103: 1570-1573 (1985).
Lazarus et al., An in vitro Method Which Assesses Corneal Epithelial Toxicity due to Antineoplastic,Apreservative and Antimicrobial Agents, *Lens Eye Toxic. Res.* 6: 59-85 (1989).
Leeming, Treatment of Ocular Infections with Topical Antibacterials, *Clin. Pharmacokinet.* 37: 351-360 (1999).
Leibowitz et al., Human Conjunctivitis: Diagnostic Evaluation, *Arch. Ophthalmol.* 94: 1747-1749 (1976).
Lu & Chan, Flavobacterium indologenes Keratitis, *Ophthalmologica* 211: 98-100 (1997).
Satpathy & Vishalakshi, Ulcerative Keratitis: Microbial Profile and Sensitivity Pattern: A Five Year Study, *Ann. Ophthalmol. Glaucoma* 27: 301-306 (1995).
Wilkins et al., Penicillin-Resistant *Streptococcus pneumoniae* Keratitis, *Cornea* 15: 99-100 (1996).
U.S. Appl. No. 09/533,341, filed Mar. 23, 2000, Catania et al.

* cited by examiner

*Primary Examiner*—B. Dell Chism
(74) *Attorney, Agent, or Firm*—Michael J. Wise; Perkins Coie LLP (57) ABSTRACT

The present invention discloses a method of treating an ophthalmic infection by administering to a vertebrate inflicted with the ophthalmic infection an ophthalmologically effective amount of an antimicrobial peptide which is derived from alpha-melanocyte-stimulating hormone (α-MSH) and biologically functional equivalents thereof. Specifically, the antimicrobial peptides derived from alpha-melanocyte-stimulating hormone (α-MSH) include α-MSH (1–13) which is SYSMEHFRWGKPV, α-MSH (4–10) which is MEHFRWG, α-MSH (6–13) which is HFRWGKPV, α-MSH (11–13) which is KPV, and a KPV dimer. The ophthalmic infection can be caused by a microorganism which include a bacteria, a fungi or a virus. The vertebrate includes a bird and a mammal. The antimicrobial peptide has anti-bacterial, antifungal, and antiviral property and therefore can be administered at the onset of the ophthalmic infection before the microorganism causing the infection is determined as well as thereafter.

43 Claims, 7 Drawing Sheets

TREATMENT OF OPHTHALMIC INFECTIONS USING ANTIMICROBIAL PEPTIDES

CROSS-REFERENCE TO RELATED APPLICATION

This application claims the benefit of U.S. Provisional Application No. 60/382,887, filed May 21, 2002, which is incorporated by reference in its entirety including drawings as set forth herein.

TECHNICAL FIELD

The present invention relates to the treatment of ophthalmic infections using antimicrobial peptides.

BACKGROUND

Eyes are the windows of a body, open to the external world and rich in nutrients, helping a living being to perceive the surrounding environment. Consequently, eyes are vulnerable to virulent microorganisms, the invasion and uncontrolled growth of which causes various types of ophthalmic infections, for instance, blepharitis, conjunctivitis and keratitis.

The common types of microorganisms causing ophthalmic infections are viruses, bacteria, and fungi. These microorganisms may directly invade the surface of the eye, or permeate into the globe of the eye through trauma or surgery, or transmit into the eye through the blood stream or lymphatic system as a consequence of a systemic disease. The microorganisms may attack any part of the eye structure, including the conjunctiva, the cornea, the uvea, the vitreous body, the retina, and the optic nerve.

Ophthalmic infections can cause severe pain, swollen and red tissues in or around eyes, and blurred or decreased vision and warrant immediate medical treatment. However, before the nature of the microorganism causing the infections is first determined, initial treatment options at the onset of the infections are usually very limited, since the differentiation of a bacteria-caused ophthalmic infection from virus-caused or fungi-caused infection on the basis of clinical observation is frequently not reliable. Leibowitz et al., *Human Conjunctivitis: Diagnostic Evaluation, Arch. Ophthalmol.* 94: 1747–1749 (1976). Once the microorganism data are available after days of the infections, the ophthalmic infections can then be treated with pertinent antimicrobial agents, including antiviral agents, antibacterial agents or antifungal agents, individually or in combination.

The antiviral agents commonly used in treating ophthalmic infections are Idoxurine and Acyclovir. Idoxurine inhibits the replication of viral DNA and is effective against *Herpes simplex* virus (HSV). However, studies have shown that Idoxurine is toxic to corneal epithelial cells and if the treatment continues for longer than a week it may cause punctate lesions to develop. Lazarus et al., *An in vitro Method Which Assesses Corneal Epithelial Toxicity due to Antineoplastic, Apreservative and Antimicrobial Agents, Lens Eye Toxic. Res.* 6: 59–85 (1989). Acyclovir inhibits DNA replication of *Herpes zoster* virus (HZV) and therefore is commonly used to HZV-caused blepharitis or keratitis. However, it has been reported that Acyclovir has little or no preventative effect on the ocular complications of HZV. Aylad et al., *Influence of Oral Acyclovir on Ocular Complications of Herpes zoster ophthalmicus, Eye* 8: 70–74 (1994).

The majority of bacteria-caused ophthalmic infections are treated with topically applied ophthalmic antibacterial agents, including sulphonamide, tetracycline, chloramphenicol, aminoglycoside, beta-lactam, vancomycin, and fluoroquinolone. Leeming, *Treatment of Ocular Infections with Topical Antibacterials, Clin. Pharmacokinet.* 37: 351–360 (1999). However, considerable resistance to the antibacterial agents has been reportedly developed in bacteria. Studies have shown that 75% of ocular *Staphylococcus* species are resistant to tetracycline. Doughtery et al., *The Role of Tetracycline in Chronic Blepharitis: Inhibition of Lipase Production in Staphylococcus, Inv. Ophthalmol. Vic. Sci.* 32: 2970–2975 (1991). *Flavobacterium indologenes* is now resistant to most antibacterial agents. Lu & Chan, *Flavobacterium indoloqenes Keratitis, Ophthalmologica* 211: 98–100 (1997). *Streptococcus pneumoniae* and some strains of *pneunococcus* are resistant to penicillin. Wilkins et al., *Penicillin-Resistant Streptococcus pneumoniae Keratitis, Cornea* 15: 99–100 (1996). Approximately one third of *Staphylococcus* strains are resistant to gentamycin. Huberspitz et al., *Corneal Ulceration: An Update from a Specialized Ambulatory Care Centre, Klinische. Monals. Augen.* 200: 251–256 (1992). Additionally, 50% of bacteria isolated from corneal ulcers are resistant to all the common antibacterial agents. Satpathy & Vishalakshi, *Ulcerative Keratitis: Microbial Profile and Sensitivity Pattern: A Five Year Study, Ann. Ophthalmol. Glaucoma* 27: 301–306 (1995).

Antifungal agents are classified into two groups: polyenes such as amphotericin-B and azoles such as fluconazole. However, amphotericin-B is reported to have poor penetration into ocular tissues and show toxicity against eyes. Ishibashi & Kaufman, *The Effects of Subconjunctival Miconozole in the Treatment of Experimental Candida Keratitis in Rabbits, Arch. Ophthalmol.* 103: 1570–1573 (1985). Resistance to azoles and amphotericin-B has also been reported. Armstrong, *The microbiology of the Eye, Ophthal. Physiol. Opt.* 20: 429–503 (2000).

Given that the toxicity and resistance are commonly associated with the treatment of ophthalmic infections using the existing antimicrobial agents, it is desirable to provide a method for the treatment of ophthalmic infections using an inventive antimicrobial agent to reduce or minimize the toxicity and resistance. It is also desirable to provide a method for the treatment of an ophthalmic infection using an inventive antimicrobial agent that has antiviral, antibacterial and antifungal properties and can be used to treat the ophthalmic infection immediately after the onset of the infection without first taking days to determine the nature of microorganism causing the infection.

SUMMARY

The primary aspect of the present invention is directed to a method of treating an ophthalmic infection in a vertebrate inflicted with the ophthalmic infection which comprises administering an ophthalmologically effective amount of an antimicrobial peptide to the vertebrate.

According to one embodiment of the invention, the antimicrobial peptide is selected from the group of peptides with an amino acid sequence consisting of KPV, MEHFRWG (SEQ ID NO: 1), HFRWGKPV (SEQ ID NO: 2), SYSME-HFRWGKPV (SEQ ID NO: 3), a KPV dimer and a biologically functional equivalent thereof.

According to another embodiment of the invention, the ophthalmic infection is a bacterial ophthalmic infection, a fungal ophthalmic infection or a viral ophthalmic infection.

According to another embodiment of the invention, the antimicrobial peptide is administered through a conjunctival administration, a nasal administration, a buccal administration an oral administration, a rectal administration, a vaginal administration, an epidermal administration, and a parenteral administration.

According to another embodiment of the invention, the antimicrobial peptide can be administered at the onset of the ophthalmic infection before a microorganism causing the ophthalmic infection is determined or after the microorganism causing the ophthalmic infection is determined.

According to another embodiment of the invention, the antimicrobial peptide can be administered individually, or with another antimicrobial peptide, or with an existing antimicrobial agent, or with a non-antimicrobial agent.

BRIEF DESCRIPTION OF THE DRAWINGS

The accompanying figures of the drawing are incorporated into and form a part of the specification to provide illustrative examples of the present invention and to explain the principles of the invention. The figures of the drawing are only for purposes of illustrating preferred and alternate embodiments of how the invention can be made and used. It is to be understood, of course, that the drawing is intended to represent and illustrate the concepts of the invention. The figures of the drawing are not to be construed as limiting the invention to only the illustrated and described examples. Various advantages and features of the present invention will be apparent from a consideration of the written specification and the accompanying figures of the drawing wherein.

DETAILED DESCRIPTION

The broadest aspect of the invention is a method for treating an ophthalmic infection using an antimicrobial peptide. A preferred embodiment of the invention is a method for treating an ophthalmic infection using an antimicrobial peptide selected from the group of peptides with an amino acid sequence consisting of KPV, MEHFRWG (SEQ ID NO: 1), HFRWGKPV (SEQ ID NO: 2), SYSMEHFRWGKPV (SEQ ID NO: 3), a KPV dimer, and a biologically functional equivalent thereof.

SYSMEHFRWGKPV (SEQ ID NO: 3) is the entire amino acid sequence of alpha-Melanocyte Stimulating Hormone (hereinafter referred to as "α-MSH" or "alpha-MSH" or "α-MSH [1–13]") and the first 13 amino acid sequence derived from Adrenocorticotropic Hormone (hereinafter referred to as "ACTH"). U.S. Pat. No. 5,028,592 discloses that α-MSH has anti-pyretic and anti-inflammatory properties and that α-MSH[11–13] which is KPV, the C-terminal trimer of α-MSH, is responsible for the anti-pyretic and anti-inflammatory properties of α-MSH. Since α-MSH and KPV are well disclosed and characterized in U.S. Pat. No. 5,028,592, this reference is hereby incorporated by reference in its entirety.

HFRWGKPV (SEQ ID NO: 2) is the amino acid sequence of α-MSH from residue 6 through residue 13, which is also referred to as α-MSH[6–13]. MEHFRWG (SEQ ID NO: 1) is the amino acid sequence of α-MSH from residue 4 through residue 10, which is also referred to as α-MSH [4–10]. U.S. patent application Ser. No. 09/533,341, entitled "Antimicrobial and anti-inflammatory peptides for use in human immunodeficiency virus," disclosed that peptides KPV, MEHFRWG (SEQ ID NO: 1), HFRWGKPV (SEQ ID NO: 2), and SYSMEHFRWGKPV (SEQ ID NO: 3) have anti-viral, anti-bacterial and anti-fungal properties. U.S. patent application Ser. No. 09/533,341 is hereby incorporated by reference in its entirety.

The KPV dimer is formed when the N-terminals of two PKV peptides are linked by a linker. For example, VPKC-s-s-CKPV (SEQ ID NO: 4), one kind of the KPV dimers, is formed by adding a cystein at the N-terminal of KPV peptide and allowing-the cysteins of two CKPV (SEQ ID NO: 5) peptides to form a disulfide bond (-s-s-). In another word, VPKC-s-s-CKPV (SEQ ID NO: 4) is formed when two KPV peptides are linked by a -Cys-s-s-Cys-linker. The linker can be any kind of chemical bonds that links the N-terminals of two KPV peptides together. It is preferred that the linker be -Cys-s-s-Cys-, -DCys-s-s-Cys-, -Pen-s-s-Cys-, -Pen-s-s-DCys-, -DPen-s-s-Cys-, -DPen-s-s-DCys-, -DPen-s-s-DPen-, -Pen-s-s-Pen-, -hCys-s-s-Cys-, -hCys-s-s-DCys-, -hCys-s-s-hCys-, -DhCys-s-s-DhCys-, -DhCys-s-s-hCys-, -hCys-s-s-Pen-, -hCys-s-s-DPen-, or -DhCys-s-s-DPen-. It is more preferred that the linker be -Cys-Cys-. The term "Pen" refers to Penicillamine. The Term "Cys" refers to Cysteine. The Term "hCys" refers to Omocysteine. The prefix "D" refers to the detro-form of an amino acid. Accordingly, it is preferred that the KPV dimer be VPK-Cys-s-s-Cys-KPV (SEQ ID NO: 4), VPK-DCys-s-s-Cys-KPV, VPK-Pen-s-s-Cys-KPV (SEQ ID NO: 6), VPK-Pen-s-s-DCys-KPV, VPK-DPen-s-s-Cys-KPV, VPK-DPen-s-s-DCys-KPV, VPK-DPen-s-s-DPen-KPV, VPK-Pen-s-s-Pen-KPV (SEQ ID NO: 7), VPK-hCys-s-s-Cys-KPV (SEQ ID NO: 8), VPK-hCys-s-s-DCys-KPV, VPK-hCys-s-s-hCys-KPV (SEQ ID NO: 9), VPK-DhCys-s-s-DhCys-KPV, VPK-DhCys-s-s-hCys-KPV, VPK-hCys-s-s-Pen-KPV (SEQ ID NO: 10), VPK-hCys-s-s-DPen-KPV, or VPK-DhCys-s-s-DPen-KPV. It is more preferred that the KPV dimer be VPK-Cys-s-s-Cys-KPV (SEQ ID NO: 4).

The biological functional equivalent is defined as an amino acid sequence that is functionally equivalent to KPV, VPKC-s-s-C-KPV (SEQ ID NO: 4), MEHFRWG (SEQ ID NO: 1), HFRWGKPV (SEQ ID NO: 2), and SYSMEHFR-WGKPV (SEQ ID NO: 3) in terms of biological activity. Although the specific amino acid sequences described here are effective, it is clear to those familiar with the art that amino acids can be substituted in the amino acid sequence or deleted without altering the effectiveness of the peptides. Further, it is known that stabilization of the α-MSH sequence can greatly increase the activity of the peptide and that substitution of D-amino acid forms for L-forms can improve or decrease the effectiveness of peptides. For example, a stable analog of α-MSH, [Nle$^4$, D-Phe$^7$], α-MSH, which is known to have marked biological activity on melanocytes and melanoma cells, is approximately ten times more potent than the parent peptide in reducing fever. Holdeman, M. and Lipton, J. M., *Antipyretic Activity of a Potent α-MSH Analog*, Peptides 6, 273–5:(1985). Further, adding amino acids to the C-terminal α-MSH (11–13) sequence can reduce or enhance antipyretic potency (Deeter, L. B.; Martin, L. W.; Lipton, J. M., *Antipyretic Properties of Centrally Administered α-MSH Fragments in the Rabbit*, Peptides 9, 1285–8 (1989). Addition of glycine to form the 10–13 sequence slightly decreased potency; the 9–13 sequence was almost devoid of activity, whereas the potency of the 8–13 sequence was greater than that of the 11–13 sequence. It is known that Ac-[D-K$^{11}$] α-MSH 11–13-NH$_2$ has the same general potency as the L-form of the tripeptide α-MSH 11–13. Hiltz, M. E.; Catania, A.; Lipton, J. M., *Anti-inflammatory Activity of α-MSH (11–13) Analogs: Influences of Alterations in Stereochemistry*, Peptides 12, 767–71 (1991). However, substitution with D-proline in position 12 of the tripeptide rendered it inactive. Substitution with D-proline in position 12 of the tripeptide rendered it inactive. Substitution with the D-form of valine in position 13 or with the D-form of lysine at position 11 plus the D-form of valine at position 13 resulted in greater anti-inflammatory activity than with the L-form tripeptide. These examples indicate that alterations in the amino acid characteristics of the peptides can influence activity of the peptides or have little effect, depending upon the nature of the manipulation. It is also believed that biological functional equivalents may be obtained by substitution of amino acids having similar hydropatbic values. Thus, for example, iso-leucine and leucine, which have a hydropathic index +4.5 and +3.8, respectively, can be substituted for valine, which has a hydropathic index of +4.2, and still obtain a protein having like biological activity. Alternatively, at the other end of the scale, lysine (–3.9) can be substituted for arginine (–4.5), and so on. In general, it is believed that amino acids can be successfully substituted where such amino acid has a hydropathic score of within about +/–1 hydropathic index unit of the replaced amino acid. The antimicrobial properties of biological functional equivalents can be measured through their inhibitory effect on the colony forming units in bacteria or fungi, or through their inhibitory effect on the HIV expression or transcription, as disclosed in the examples of the description of this invention.

Figure 1:
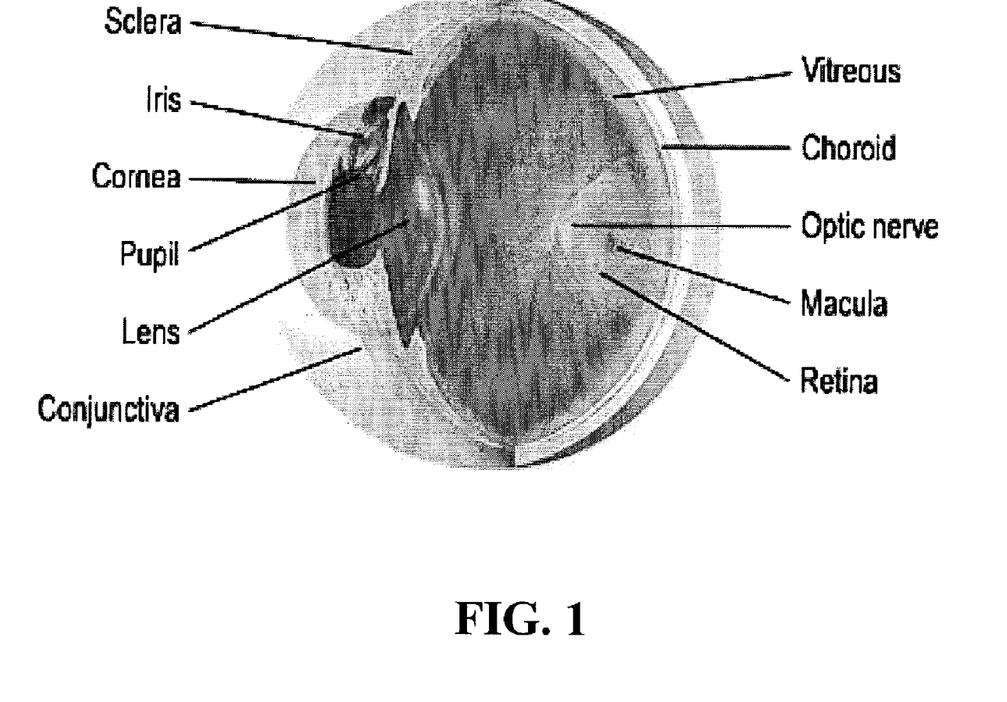
FIG. 1. The anatomy of a human eye. The human eye structure includes conjunctiva, cornea, vitreous body, retina, and optic nerve.
Figure 2:
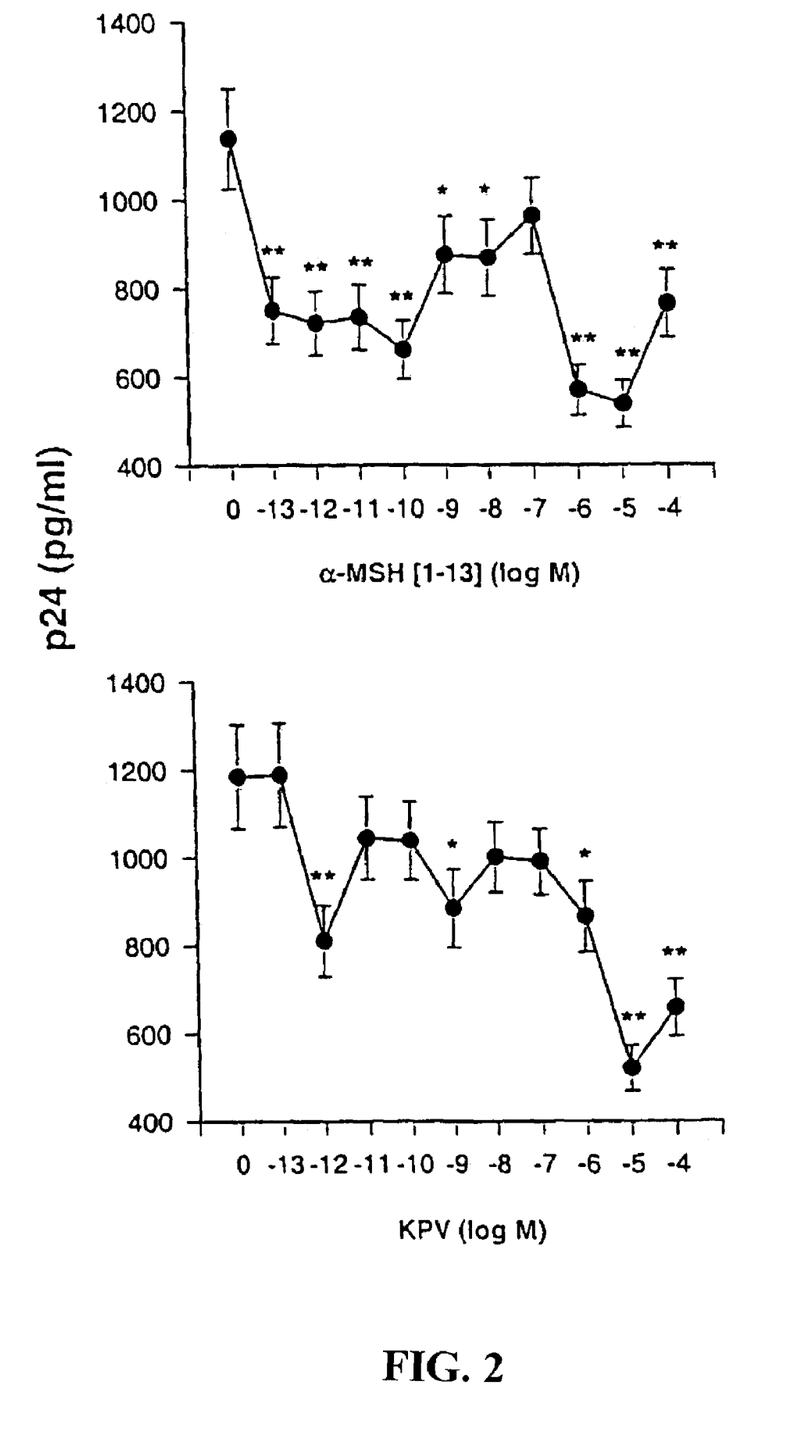
FIG. 2. The effect of α-MSH [1–13] which is SYSMEHFRWGKPV (SEQ ID NO: 3) or α-MSH [11–13] which is KPV on p24 release by TNF-α stimulated U1 cells. Both α-MSH [1–13] and KPV peptides inhibited p24 release over a broad spectrum of concentrations. In this and following figures, columns or dots represent the mean and bars represent the standard deviation or confidence interval when p<0.05(*) or p<0.01(**).
Figure 3:
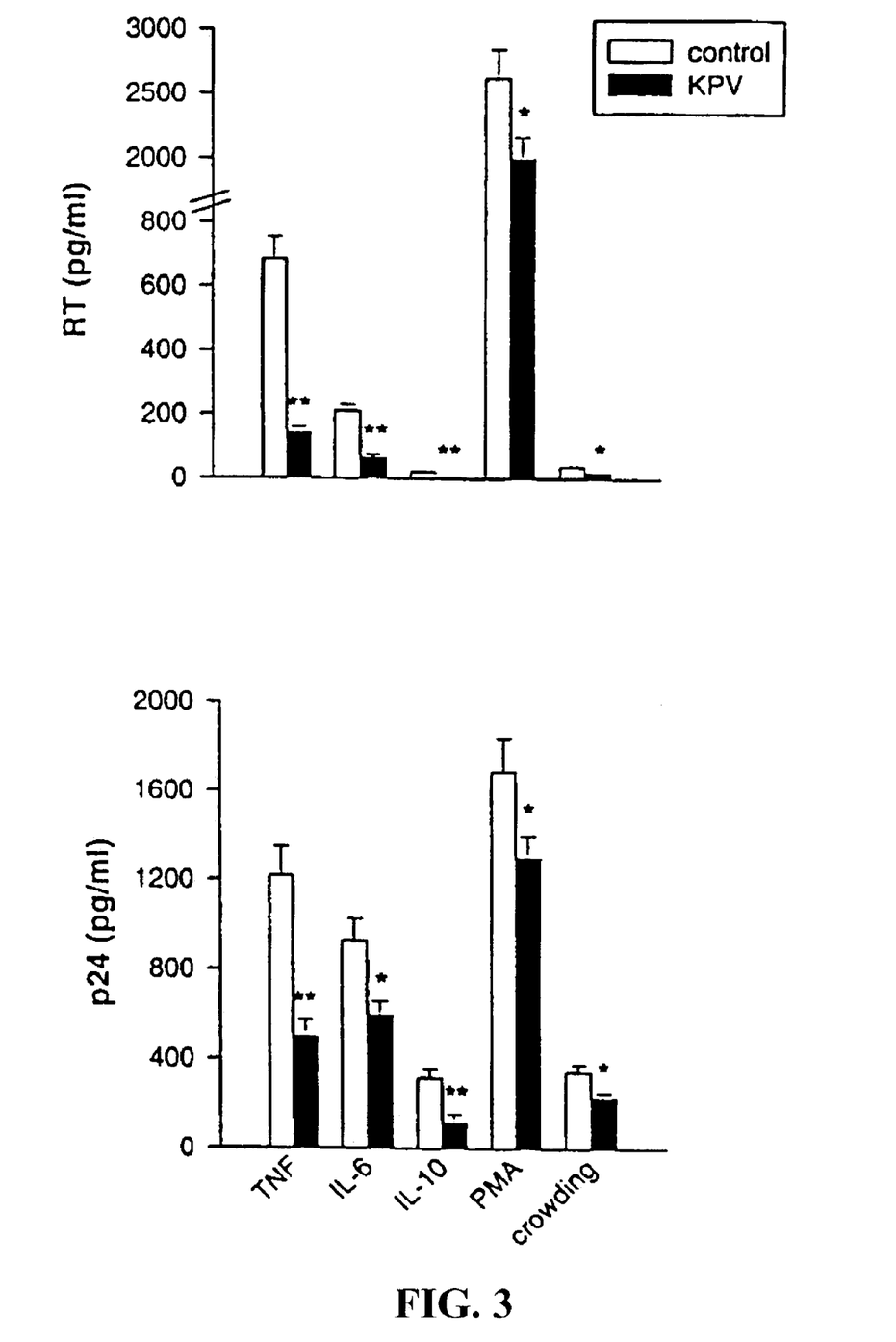
FIG. 3. The effect of KPV on RT and p24 release by stimulated U1 cells. Treatment with KPV ($10^{-5}$ M) inhibited HIV reverse transcriptase (RT) and p24 release from U1 cells exposed to different stimuli.

The ophthalmic infection of this invention refers to an infection caused by a microorganism or microorganisms in or around an eye or the eye structure which include the eyelids and lacrimal apparatus, the conjunctiva, the cornea, the uvea, the vitreous body, the retina, and the optic nerve. FIG. 1. Based on the nature of the microorganism, the ophthalmic infection includes a bacterial ophthalmic infection, a fungal ophthalmic infection, and a viral ophthalmic infection.

The bacterial ophthalmic infection of the invention includes Blepharitis, Hordeolum, Preseptal Cellulitis, Dacryocystitis, Orbital Cellulitis, Erysipelas, Vernal Keratoconjunctivitis, Bacterial Conjunctivitis, Conjunctival Laceration, Superior Limbic Keratoconjunctivitis, Conjunctivitis with Pseudomembrane, Epidemic Keratoconjunctivitis, Bacterial Keratitis, Corneal Ulceration, Phlyctenulosis, Anterior Uveitis, Endophthalmitis, Bacterial Abscess, Acute Spetic Retinitis, Chronic Bacterial Retinitis, Papillitis, Optic Neuritis, and Orbital Cellulitis. It is preferred that the bacterial ophthalmic infection be Blepharitis, Bacterial Conjunctivitis, and Bacterial Keratitis.

The bacterial ophthalmic infection of the invention can be caused by *Staphylococcus, Streptococcus, Treponema, Pneumococcus, Gonococcus, Haemophilus, Klebsiella, Neisseria, Chlamydia, Mycobacterium, Flavobacterium, Serratia, Propionibacterium, Actinomyces, Pseudomonas, Corynebacterium, Meningococcus,* and *Euterococcus.* It is preferred that the bacterial ophthalmic infection be caused by *Staphylococcus, Streptococcus,* and *Eutercoccus.* It is more preferred that the bacterial ophthalmic infection be caused by *Staphylococcus* and *Streptococcus.* The key species of *Staphylococcus* and *Streptococcus* genus are *Staphylococcus saureus, Staphylococcus epidermidis, Streptococcus viridans,* and *Streptococcus pneumoniae.*

The viral ophthalmic infection of the invention includes Herpes Zoster Ophthalmicus, Herpes Simplex Blepharitis, Verruca, Molluscum Contagiosum, Infective Mononucleosis, Viral Conjunctivitis, Episcleritis, Scleritis, Herpes Simplex Keratitis, Iridocyclitis, Ocular Syphilis, Cytomealovirus Retinitis, and Viral Papillitis and Optic Neuritis. It is preferred the viral ophthalmic infection be Viral Conjunctivitis, Herpes Simplex Keratitis, and Cytomealovirus Retinitis.

The viral ophthalmic infection of the invention is caused by Poxvirus, Herpesvirus, Adenovirus, Paramyxovirus and Human Immunodeficiency virus. It is preferred the viral ophthalmic infection be caused by Herpesvirus and Human Immunodeficiency virus (HIV). The key species in Herpesvirus are *Herpes simplex* virus, *Herpes zoster* virus, Epstein-Barr virus, *Cytomegalovirus.*

The fungal ophthalmic infection of the invention includes Ringworm, Fungal Conjuctivitis, Keratomycosis, Uveitis, Abscess, *Candida* Retinitis, Fungal Papillitis and Optic Neuritis, Invasive Aspergillosis and Mucormycosis. The fungal ophthalmic infection is caused by *Microsporum, Trichophyton, Aspergillus, Leptothrix, Sporotrichum, Fusarium, Cephalosporium, Cryptococcus, Phycomycetes,* and *Candida*. It is preferred the fungal ophthalmic infection be caused by *Aspergillus* and *Candida*. The key species of *Aspergillus* is *Aspergillus fumigatus*. The key species of *Candida* is *Candida albicans*.

Another preferred embodiment of the invention is a method for treating an ophthalmic infection in a vertebrate using an antimicrobial peptide. The vertebrate in the invention includes a bird and a mammal. It is preferred the bird in the invention be *Columba livia* (pigeon), *Gallus domesticus* (chicken), and *Meleagris gallopavo* (turkey). It is preferred the mammal in the invention be *Primates, Carnivora, Proboscidea, Perissodactyla, Artiodactyla, Rodentia* and *Lagomorpha*. It is more preffered that the mammal in the invention be *Canis familiaris* (dog), *Felis catus* (cat), *Elephas maximus* (elephant), *Equus caballus* (horse), *Sus domesticus* (pig), *Camelus dromedarius* (camel), *Cervus axis* (deer), *Giraffa camelopardalis* (giraffe), *Bos taurus* (cattle), *Capra hircus* (goat), *Ovis aries* (sheep), *Mus musculus* (mouse), *Lepus brachyurus* (rabbit), *Mesocricetus auratus* (hamster), *Cavia porcellus* (guinea pig), *Meriones unguiculatus* (gerbil) and *Homo sapiens* (human). It is even more preferred that the mammal in the invention be *Homo sapiens* (human).

Another preferred embodiment of the invention is a method for treating an ophthalmic infection comprising administering into a vertebrate an antimicrobial peptide. The antimicrobial peptide of this invention is administered into the vertebrate through conjunctival administration, nasal administration, buccal administration, oral administration, rectal administration, vaginal administration, epidermal administration, and parenteral administration. The conjunctival administration refers to the delivery of the antimicrobial peptide across the corneal and conjunctival surface into the eye or the rest of the body of a vertebrate. The nasal administration refers to the delivery of the antimicrobial peptide across the nasal mucous epithelium and into the peripheral circulation. The buccal administration refers to the delivery across the buccal or lingual epithelia into the peripheral circulation. The oral administration refers to the delivery of the antimicrobial peptide through the buccal epithelia but predominantly swallowed and absorbed in the stomach and alimentary tract. The rectal administration refers the delivery of the antimicrobial peptide via the lower alimentary tract mucosal membranes into the peripheral circulation. The vaginal administration refers to the delivery of the antimicrobial peptide through vaginal mucous membrane into the peripheral circulation. The epidermal administration refers to the delivery of the antimicrobial peptide across the dermis and absorption into the peripheral circulation. The parenteral administration refers to the injection of the antimicrobial peptide contained in a solution into the vertebrate. The injection in the parenteral administration can be intravenous, intramuscular, subcutaneous, subconjunctival, intraocular, retrobulbar, epidural, intramedullary, and intrathecal.

It is preferred the antimicrobial peptide in this invention be administered into the vertebrate through a conjunctival administration whereas the antimicrobial peptide can be included in a form of an ophthalmic solution, an ophthalmic suspension, an ophthalmic gel, an ophthalmic ointment or an ophthalmic strip/insert. The ophthalmic solution is an aqueous or organic solution formulated to use as eye drops. The ophthalmic suspension is the addition of a small particle, e.g., microfine nano-particles, which contains the antimicrobial peptide, into an aqueous or organic solution. The ophthalmic gel is a special polymer that disperses in the tear film and forms a essentially transparent film across the ocular surface. The ophthalmic ointment is a mixture of a petrolatum base with wool fat. The ophthalmic strip/insert refers to a filter paper or insoluble contact lens-like object which can be impregnated with the antimicrobial peptide. The impregnated ophthalmic strip/insert can then be place onto the ocular surface or inserted into the lower cul-de-sac.

Another preferred embodiment of the invention is a method for treating an ophthalmic infection in a vertebrate using an ophthalmologically effective amount of an antimicrobial peptide. The ophthalmologically effective amount is at least $10^{-12}$ Molar. It is preferred the ophthalmologically effective amount is at least $10^{-8}$ Molar. The exact ophthalmologically effective amount depends on the particular administration being used, the age, weight, and general physical conditions of the particular vertebrate being treated, the severity of the ophthalmic infection, and other antimicrobial agents being used in combination with the antimicrobial peptide, as is well known to those skilled in the art.

Another preferred embodiment of the invention is a method for treating an ophthalmic infection in a vertebrate administering an ophthalmologically effective amount of an antimicrobial peptide. Since the antimicrobial peptide has antibacterial, antifungal and antiviral properties, the antimicrobial peptide can be used immediately after the ophthalmic infection is observed before the microorganism causing the infection is determined. The antimicrobial peptide can continuously be used after the microorganism causing the infection is determined.

Another preferred embodiment of the invention is a method for treating an ophthalmic infection in a vertebrate administering an ophthalmologically effective amount of an antimicrobial peptide. The antimicrobial peptide can be used individually, or in combination with another antimicrobial peptide, or in combination with other antimicrobial agent which is not an antimicrobial peptide, or in combination with a non-antimicrobial agent in treating the ophthalmic infection.

EXAMPLES

Example I

The Antimicrobial Peptides

Figure 6:
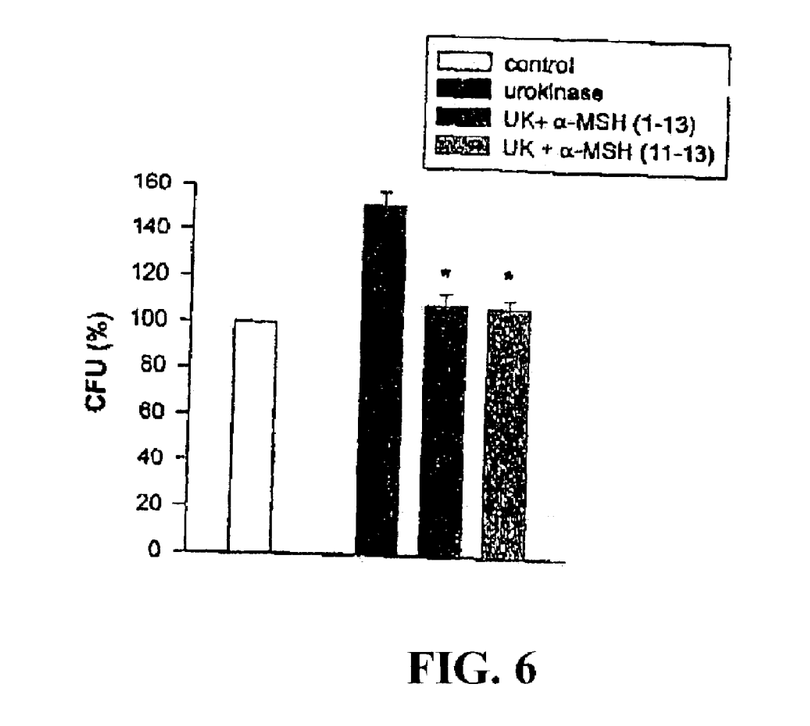
FIG. 6. The effect of α-MSH [1–13] which is SYSMEHFRWGKPV (SEQ ID NO: 3), α-MSH [11–13] which is KPV, and the "KPV dimer" which is VPKC-s-s-CKPV (SEQ ID NO: 4) on *S. aureus* colony forming units when *S. aureus*' growth is enhanced by urokinase. The treatment with urokinase increases *S. aureus* colony formation, but the addition of α-MSH [1–13] or α-MSH [11–13] (KPV) significantly inhibited this urokinase-enhancing effect.
Figure 9:
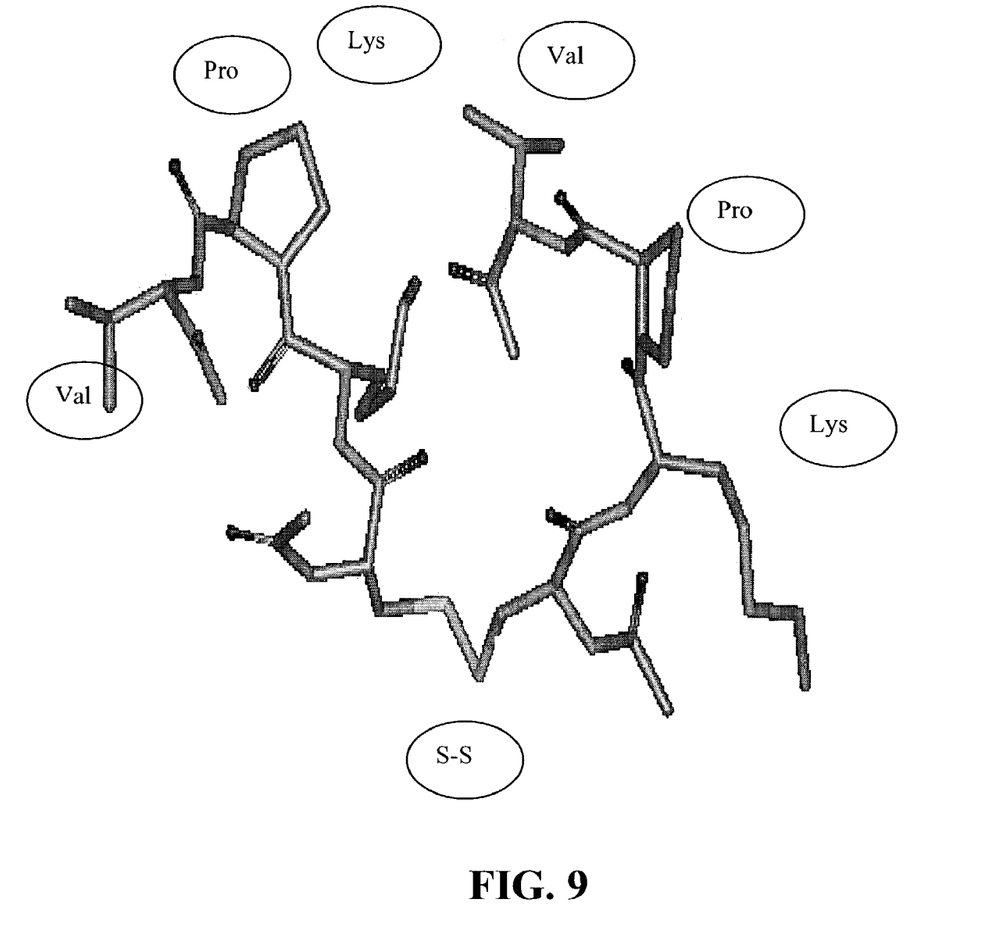
FIG. 9. Molecular conformational structure of the KPV dimer which is VPKC-s-s-CKPV (SEQ ID NO: 4). Molecular modeling study revealed the conformational structure of the KPV dimer. VPKC-s-s-CKPV (SEQ ID NO: 4) adopts a like-β-turn-structure well organized and stabilized by intramolecular hydrogen bounds. The tertiary structure of the dimer is folded and amino acids are well protected. It also resembles a cyclic peptide with a beta-turn.

The antimicrobial peptides used in the examples included: α-MSH (1–13) which is SYSMEHFRWGKPV (SEQ ID NO: 3), α-MSH (4–10) which is MEHFRWG (SEQ ID NO: 1), α-MSH (6–13) which is HFRWGKPV (SEQ ID NO: 2), and α-MSH (11–13) which is KPV, all of which were N-acetylated and C-amidated, and ACTH (1–39) and ACTH (18–39) which is also called CLIP. The peptides were prepared by solid-phase peptide synthesis and purified by reversed-phase high performance liquid chromatography. Another peptide used in this research included a dimer of the amino acid sequence KPV, specifically VPKCCKPV (SEQ ID NO: 4), which also was N-acetylated and C-amidated (the "KPV dimer"). The VPKCCKPV (SEQ ID NO: 4) can be chemically represented as Val-Pro-Lys-AcCys-s-s-CysAc-Lys-Pro-Val (SEQ ID NO: 11) or VPKC-s-s-CKPV (SEQ ID NO: 4). The VPKCCKPV (SEQ ID NO: 4) is formed by adding cysteins at the N-terminal of KPV peptide and allowing the cysteins of two CKPV (SEQ ID NO: 5) peptide to form a disulfide bond. As shown in FIG. 9, the molecular conformation of the VPKC-s-s-CKPV (SEQ ID NO: 4) was studied through molecular modeling techniques. The molecular modeling study were performed using the SYBYL software version 6.2 running on Silicon Graphic Indingo 2 workstation. The conformational study showed that the VPKCCKPV (SEQ ID NO: 4) peptide adopts a like-β-turn-structure well organized and stabilized by intramolecular hydrogen bounds. The dimer is something in-between a peptide and a peptidomimetic. The tertiary structure of the dimer is folded and amino acids are well protected. It also resembles a cyclic peptide with a beta-turn.

Example II

The Antimicrobial Peptides Inhibit HIV-p24 Expression in HIV Infected Cells.

The chronically HIV-1 infected promonocytic UI cell line was maintained in complete culture medium (RPMI 1640 supplemented with 10 mM Hepes), 2 mM L-glutamine (Sigma-Aldrich), 10% heat-inactivated FCS (HyClone Laboratories, Logan, Utah, USA), penicillin at 100 units/mL and streptomycin at 100 μg/mL (Gibco Laboratories, Grand Island, N.Y.) in log phase of growth. Before use, cells were washed three times with HBSS (Gibco) to remove extracellular virus. Cells were plated onto 24-well flat-bottomed plates at a concentration of 2×10/mL (final volume 1 mL) with medium plus TNF-α (10 ng/mL (R&D Systems, Oxford, England, UK) in the presence or absence of α-MSH or KPV in concentrations from $10^{-13}$ to $10^{-4}$ M. Supernatants were removed by centrifugation after 48 hr incubation at 37° C. in 5% $CO_2$, and tested for HIV-p24 release. p24 antigen releases (Cellular Products Inc. Buffalo, N.Y., USA) were determined using commercial ELISA kits. In all experiments each condition was tested in triplicate.

HIV-p24 is a capside HIV structure protein. The level of HIV-p24 reflects HIV infection and HIV viral amount. As shown in FIG. 2, α-MSH (SYSMEHFRWGKPV; SEQ ID NO: 3) and the tripeptide KPV significantly inhibited p24 release from TNF-α-stimulated U1 cells. Inhibitory effects of α-MSH occurred over a broad range of peptide concentrations including picomolar concentrations that occur in human plasma. Greater concentrations caused more pronounced HIV inhibition, with the most effective concentration for both peptides being $10^{-5}$ M. In this concentration, α-MSH and KPV caused 52.7% and 56.0% inhibition of p24 release, respectively.

Example III

The Antimicrobial Peptides Inhibit HIV-p24 and Reverse Transcriptase Expression in HIV Infected Cells Stimulated by TNF-α, IL-6, IL-10, and PMA The chronically HIV-1 infected promonocytic UI cells were plated onto 24-well flat-bottomed plates at a concentration of 2×10/mL (final volume 1 mL) with medium alone or TNF-α (10 ng/mL), IL-6 (20 ng/mL), IL-10 (20 ng/mL (R&D Systems) or PMA (Ing/mL) (Sigma-Aldrich Chemicals, St. Louis, Mo., USA) in the presence or absence of KPV in concentrations of $10^{-5}$ M. Supernatants were removed by centrifugation after 48 hr incubation at 37° C. in 5% $CO_2$, and tested for HIV-P24 release and reverse transcriptase release. In crowding experiments, UI cells were seeded at the density of $2\times10^5$ mL and maintained in culture at 37° C. in 5% $CO_2$ without change of medium for 7 days. KPV in concentration of $10^{-5}$M were added on day 1. p24 antigen releases (Cellular Products Inc. Buffalo, N.Y., USA) and reverse transcriptase (ELISA Retrosys RT assay, Innovagen, Lund, Sweden) were determined using commercial ELISA kits. In all experiments each condition was tested in triplicate. As shown in FIG. 3, KPV significantly inhibited p24 and RT release from UI cells induced by IL-6, IL-10, PMA, and in crowding condition.

Example IV

The Antimicrobial Peptides Inhibit HIV Transcription.

To determine the influence of KPV on HIV transcription, $20\times10^6$ UI cells (at a density of $2\times10^5$/mL in complete medium) were stimulated for 24 h with PMA (1 ng/mL) in the presence or absence of KPV $10^{-5}$M. Total RNA was extracted by the guanidine thiocyanate phenol method using an RNA isolation kit (Tripure, Boehringer Mannheim, Indianapolis, Ind.), following the manufacturer's instructions. Ten μg of total RNA were separated by 0.8% agarose/formaldehyde gel electrophoresis and transferred onto nylon membrane. The filters were baked and hybridized for 18 hr with $\alpha^{32}$ P-labeled HIV-full length probe (kind gift of L. Turchetto and E. Vicenzi, S. Raffaele Hospital, Miian, Italy). The radiolabelling reaction was performed using a DNA labelling kit (Ready-to-go, Pharmacia Biotech, San Francisco, Calif.). Filters were washed and exposed to X-ray film for 5 days. The labeled probe was removed by washing at 80° C. in 0.1×SSC containing 0.1% sodium dodecyl sulphate and then rehybridized with $\alpha^{32}$ P-labeled glyceraldehyde-3-phosphate dehydrogenase (GAPDH) cDNA probe. Densitometric analysis was performed using ImageMaster™ VDS 3.0 software (Pharmacia Biotech) and results were expressed as density units. As shown in FIG. 4, the inhibitory activity of KPV on HIV transcription was confirmed by Northern blot analysis of HIV-RNA in PMA-stimulated UI cells. Addition of KPV reduced by approximately 50% both spliced and unspliced HIV-1 RNA in PMA-stimulated UI cells.

Example V

The Antimicrobial Peptides Severely Decrease the Viability of *Staphylococcus aureus.*

*Staphylococcus aureus* (ATCC29213) was obtained from the collection of the Department of Microbiology, Ospedale Maggiore di Milano. *S. aureus* ($1\times10^6$/ml in HBSS) was incubated in the presence or absence of α-MSH [1–13], α-MSH [11–13] which is KPV, or the "KPV dimer" at concentrations in the range of $10^{-15}$ to $10^{-4}$M for 2 hours at 37° C. *S. aureus* were then washed in cold distilled water and diluted with HBSS to a concentration of 100 organisms/ml. One ml aliquots were dispensed on blood agar plates and incubated for 24 hours at 37° C. Organism viability was estimated from the number of colony forming units. As shown in FIG. 5, α-MSH [1–13] and α-MSH [1–13] (KPV) inhibited *S. aureus* colony formation. The KPV dimer also inhibited *S. aureus* colony formation. The inhibitory effect occurred over a wide range of concentrations and was statistically significant ($p<0.01$) with peptide concentrations of $10^{-12}$ to $10^{-4}$M.

Example VI

The Antimicrobial Peptides Severely Decrease the Viability of Urokinase-induced Growth-enhanced *Staphylococcus aureus.*

In this experiment, the influence of α-MSH on urokinase-induced growth-enhancement is determined. Hart, D. A.; Loule, T.; Krulikl, W.; Reno, C., *Staphylococcus Aureus* Strains Differ in Their in Vitro Responsiveness to Human Urokinase: Evidence that Methicillin-Resistant Strains are Predominantly Nonresponsive to the Growth-Enhancing Effects of Urokinase, *Can. J. Microbiol.* 42, 1024–31 (1966). *S. aureus* ($10^5$/100 ml) were incubated for four hours at 37° C. with recombinant human urokinase 500 U (Lepetit, Milan, Italy) in a shaking water bath, in the presence or absence of α-MSH [1–13] (SYSMEHFRWGKPV; SEQ ID NO: 3) or α-MSH [11–13] (KPV) at $10^{-6}$ M. Appropriate dilutions of *S. aureus* were dispensed on agar plates and colonies counted after 24 hours incubation at 37° C. As shown in FIG. 6, the treatment with urokinase increased *S. aureus* colony formation and addition of α-MSH [1–13] or α-MSH [11–13] which is KPV at concentrations of $10^6$M significantly inhibited the enhancing effect of urokinase.

Example VII

The Antimicrobial Peptides Severely Decreases the Viability of *Candida albicans*.

Figure 7:
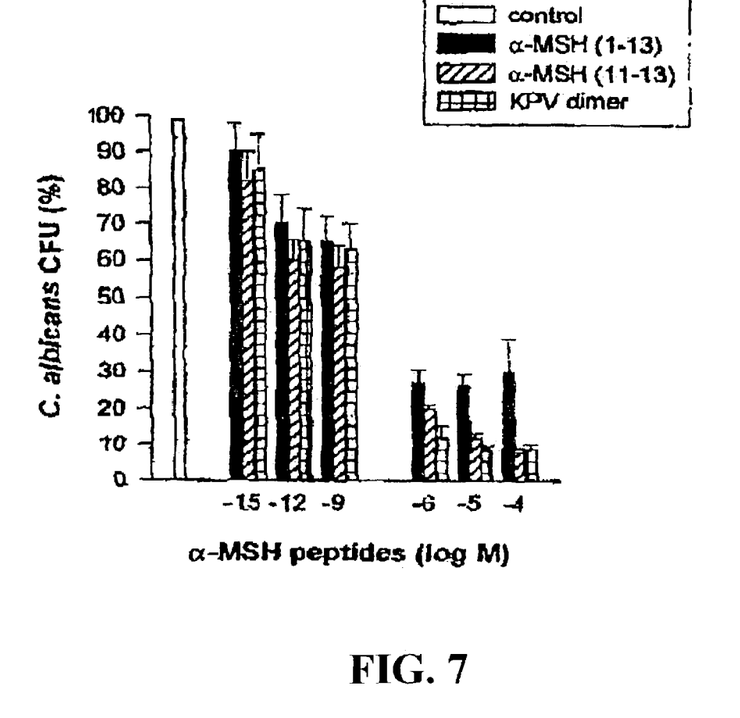
FIG. 7. The effect of α-MSH [1–13] which is SYSMEHFRWGKPV (SEQ ID NO: 3), α-MSH [11–13] which is KPV, and the "KPV dimer" which is VPKC-s-s-CKPV (SEQ ID NO: 4) on *C. albicans* colony forming units ("CFU") compared to controls. All three molecules significantly decreased *C. albicans* colony forming units over a broad range of peptide concentrations.

*C. albicans* (clinical isolate) were obtained from the collection of the Department of Microbiology, Ospedale Maggiore di Milano. *C. albicans* were maintained on Sabouraud's agar slants and periodically transferred to Sabouraud's agar plates and incubated for 48 hours at 28° C. To prepare stationary growth phase yeast, a colony was taken from the agar plate and transferred into 30 ml Sabouraud-dextrose broth and incubated for 72 hours at 32° C. Cells were centrifuged at 100×g for 10 minutes and the pellet was washed twice with distilled water. Cells were counted and suspended in Hank's balanced salt solution ("HBSS") to the desired concentration. Viability, determined by the exclusion of 0.01% methylene blue, remained >98%. *C. albicans* was then ($1\times10^6$/ml in HBSS) was incubated in the presence or absence of α-MSH [1–13], α-MSH [11–13] which is KPV, or the "KPV dimer"at concentrations in the range of $10^{-15}$ to $10^4$M for 2 hours at 37° C. Cells were then washed in cold distilled water and diluted with HBSS to a concentration of 100 organisms/ml. One ml aliquots were dispensed on blood agar plates and incubated for 48 hours at 37° C. Organism viability was estimated from the number of colonies formed. As shown in FIG. 7, *C. albicans* colony forming units were greatly reduced by α-MSH and KPV. A dimer of the amino acid sequence KPV, specifically, VPKCCKPV (SEQ ID NO: 4) (the "KPV dimer" used in FIG. 7) also inhibited *C. albicans* colony formation. Concentrations of all three peptides from $10^{-13}$ to $10^{-4}$M had significant inhibitory influences on CFU (p<0.01 vs. control).

Example VIII

Potency of Among the Antimicrobial Peptides in Reducing *C. albicans* Viability in Comparison with Fluconazole and ACTH.

Figure 4:
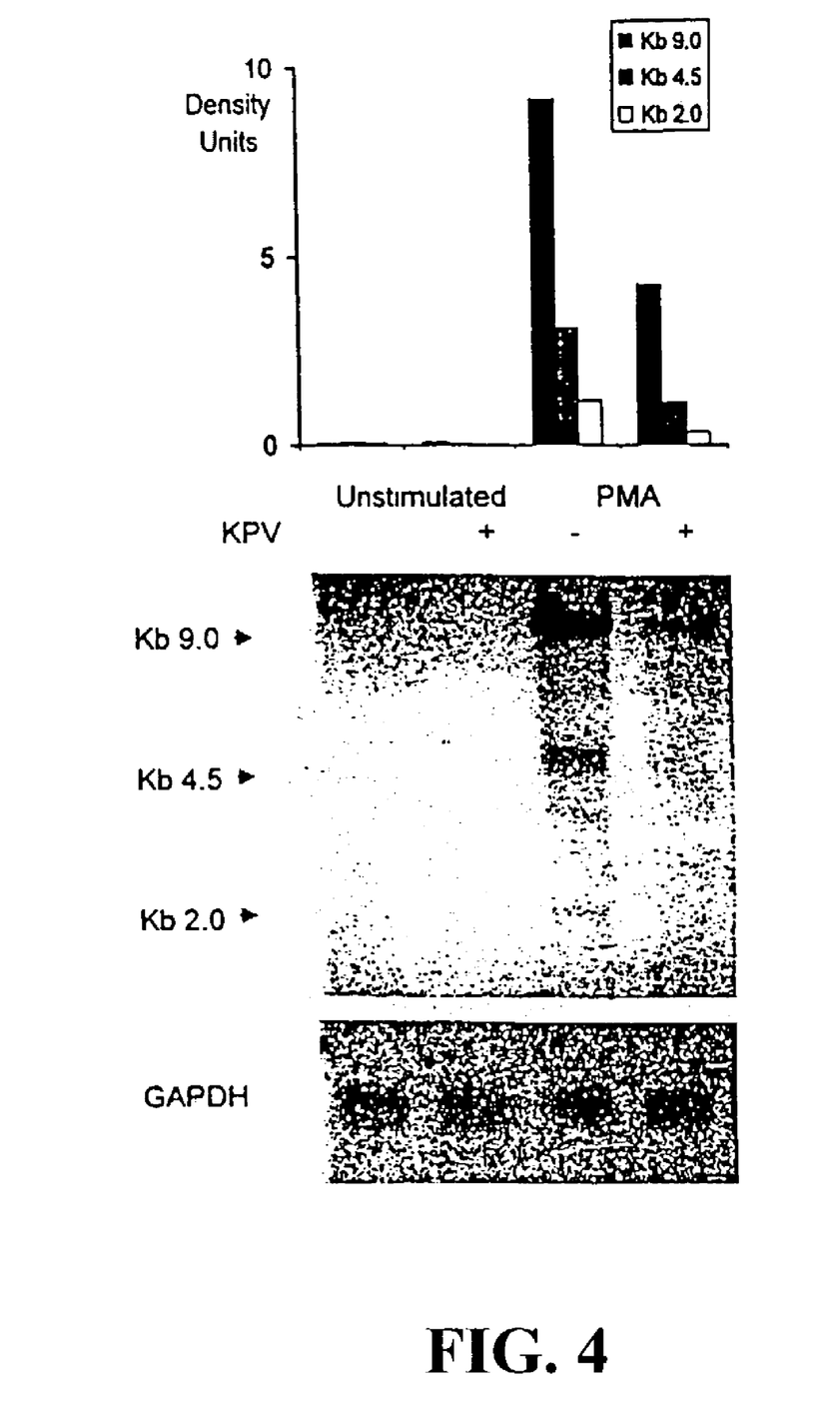
FIG. 4. The effect of KPV on HIV RNA in resting and PMA-stimulated U1 cells. Addition of KPV ($10^{-5}$M) reduced by approximately 50% both spliced and unspliced HIV-1 RNA in PMA-stimulated U1 cells.
Figure 5:
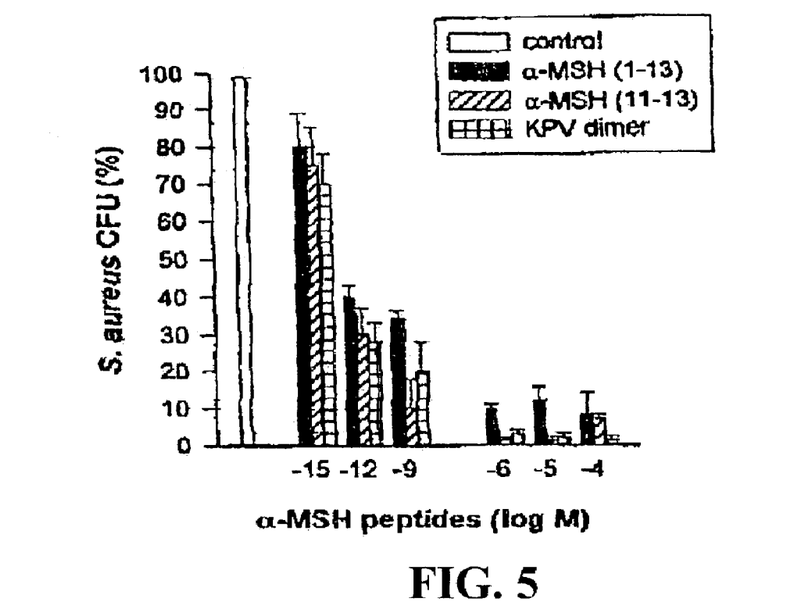
FIG. 5. The effect of α-MSH [1–13] which is SYSMEHFRWGKPV (SEQ ID NO: 3), α-MSH [11–13] which is KPV and the "KPV dimer" which is VPKC-s-s-GKPV (SEQ ID NO: 4) on *S. aureus* colony forming units ("CFU") compared to controls. All three molecules significantly decreased *S. aureus* colony forming units over a broad range of peptide concentrations.
Figure 8:
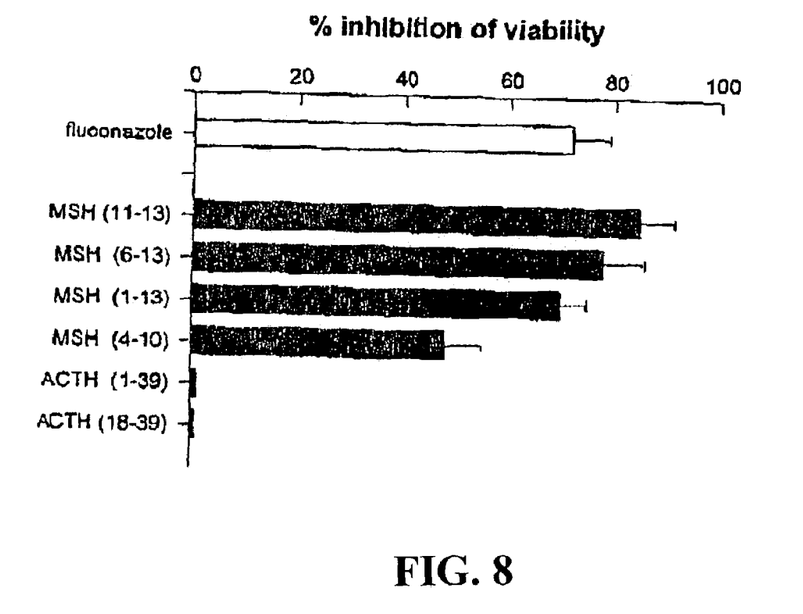
FIG. 8. A comparison of antifungal activity of certain antimicrobial peptides and fluconazole (all $10^6$M). The most effective of the antimicrobial peptides were those including the C-terminal amino acid sequence of α-MSH, for example, α-MSH [1–13] which is SYSMEHFRWGKPV (SEQ ID NO: 3), α-MSH [6–13] which is HFRWGKPV (SEQ ID NO: 2), and α-MSH [11–13] which is KPV.

Fluconazole is a well established antifungal agent. The potency of the antimicrobial peptides in reducing *C. albicans* viability is studied in comparison with fluconazole and ACTH using similar procedures as in Example VI. The peptides and fluconazole were tested in concentrations of $10^{-6}$ M. There were at least six replicates for each concentration of peptide. As shown in FIG. 8, α-MSH [11–13] (KPV), α-MSH [6–13] (HFRWGKPV: SEQ ID NO: 2), and α-MSH [1–13] (SYSMEHFRWGKPV: SEQ ID NO: 3) were the most effective. Their inhibitory activity was similar to that of fluconazole. The "core" α-MSH sequence which is α-MSH [4–10] or MEHFRWG (SEQ ID NO: 1) caused approximately 50% inhibition of CFU. Although this inhibitory effect was substantial (p<0.01 vs control), it was significantly less than that caused by α-MSH fragments bearing the KPV signal sequence, i.e., α-MSH [6–13] (HFRWGKPV: SEQ ID NO: 2) and α-MSH [11–13] (KPV) (p<0.01), or the parent molecule α-MSH [1–13] (SYSMEHFRWGKPV; SEQ ID NO: 3) (p<0.05). ACTH (1–39) and the ACTH fragment (18–39) did not reduce *C. albicans* viability (FIG. 4). Even higher concentrations of these ACTH peptides (up to $10^{-4}$ M) were likewise ineffective in reducing *C. albicans* CFU (results not shown in the figures).

Example IX

Treatment of Viral Ophthalmic Infection—HSV Blepharitis

A patient is diagnosed as having *Herpes simplex* virus blepharitis. A ophthalmic aqueous solution containing $10^{-5}$ M of KPV is prepared. The patient is instilled with 3–5 drops of the ophthalmic aqueous solution onto the surface of eyes four times daily for 7 days. After 7 days of treatment, the HSV blepharitis symptom is substantially reduced.

Example X

Treatment of Bacterial Ophthalmic Infection—Bacterial Keratitis

A patient presents complaining of eye pain when blinking and blurred vision. Upon examination the cornea appears subtly less transparent than normal cornea and may have ulcers on its surface. The diagnosis is infectious keratitis of bacterial etiology which is confirmed by laboratory findings. The patient is instilled with 3–5 drops of the ophthalmic aqueous solution containing $10^{-5}$ M of KPV onto the surface of eyes four times daily for 7 days. After 7 days of treatment, the patient fully recovers.

Example XI

Treatment of Fungal Ophthalmic Infection—Keratomycosis

Upon examination, a patient is diagnosed as having Keratomycosis. The patient is instilled with 3–5 drops of the ophthalmic aqueous solution containing 10–5 M of KPV onto the surface of eyes four times daily for 7 days. After 7 days of treatment, the patient fully recovers.

Example XII

Treatment of Ophthalmic Infection Before Microorganism Causing the Infection is Determined.

A patient presents complaining of reddened and swollen eyelids and the presence of mucoid secretions on the eye which interference with vision. While mucoid sample is sent to the laboratory for testing, the patient is instilled with 3–5 drops of the ophthalmic aqueous solution onto the surface of eyes four times daily for 3 days and symptoms disappears. The laboraroty test later shows that the patient is inflicted with bacterial conjunctivitis.

What is claimed is:

1. A method of treating an ophthalmic infection comprising administering an effective amount of an antimicrobial peptide to a vertebrate, wherein the vertebrate is inflicted with the ophthalmic infection, and wherein the antimicrobial peptide is selected from the group consisting of KPV, MEHFRWG (SEQ ID NO:1), HFRWGKPV (SEQ ID NO:2), SYSMEHFRWGKPV (SEQ ID NO:3), a KPV dimer, and a biologically functional equivalent thereof.

2. The method of claim 1, wherein the antimicrobial peptide is selected from the group consisting of KPV, MEHFRWG (SEQ ID NO:1), HFRWGKPV (SEQ ID NO:2), SYSMEHFRWGKPV (SEQ ID NO:3), and a KPV dimer.

3. The method of claim 1 or 2, wherein the KPV dimer is selected from the group consisting of VPK-Cys-s-s-Cys-KPV (SEQ ID NO:4), VPK-DCys-s-s-Cys-KPV, VPK-Pen-s-s-Cys-KPV (SEQ ID NO:6), VPK-Pen-s-s-DCys-KPV, VPK-DPen-s-s-Cys-KPV, VPK-DPen-s-s-D Cys-KPV, VPK-DPen-s-s-DPen-KPV, VPK-Pen-s-s-Pen-KPV (SEQ ID NO:7), VPK-hCys-s-s-Cys-KPV (SEQ ID NO:8), VPK-hCys-s-s-DCys-KPV, VPK-hCys-s-s-hCys-KPV (SEQ ID NO :9), VPK-DhCys-s-s-DhCys-KPV, VPK-DhCys-s-s-hCys-KPV, VPK-hCys-s-s-Pen-KPV (SEQ ID NO:10), VPK-hCys-s-s-DPen-KPV, and VPK-DhCys-s-s-DPen-KPV.

4. The method of claim 1, wherein the ophthalmic infection is selected from the group consisting of a bacterial ophthalmic infection, a fungal ophthalmic infection, and a viral ophthalmic infection.

5. The method of claim 4, wherein the ophthalmic infection is bacterial and comprises at least one selected from the group consisting of *Staphytococcus, Streptococcus, Treponema, Pneumococcus, Gonococcus, Haemophilus, Klebsiella, Neisseria, Chlamydia, Mycobacterium, Flavobacterium, Serratia, Propionibacterium, Actinomyces, Pseudomonas, Corynebacterium, Meningococcus,* and *Euterococcus.*

6. The method of claim 5, wherein the bacterial ophthalmic infection comprises *Staphylococcus* or *Streptococcus.*

7. The method of claim 6, wherein the bacterial ophthalmic infection comprises at least one selected from the group consisting of *Staphylococcus aureus, Staphylococcus epidermidis, Streptococcus viridans,* and *Streptococcus pneumoniae.*

8. The method of claim 4, wherein the ophthalmic infection is fungal and comprises at least one selected from the group consisting of *Microsporum, Trichophyton, Aspergillus, Leptothix, Sporotrichum, Fusarium, Cephalosporium, Cryptococcus, Phycomycetes,* and *Candida.*

9. The method of claim 8, wherein the fungal ophthalmic infection comprises *Aspergillus* or *Candida.*

10. The method of claim 9, wherein the fungal ophthalmic infection comprises *Aspergillus fumigatus* or Candida albicans.

11. The method of claim 4, wherein the ophthalmic infection is fungal and comprises at least one selected from the group consisting of Poxvirus, Herpesvirus, Adenovirus, Paramyxovirus and HIV.

12. The method of claim 11, wherein the viral ophthalmic infection comprises at least one selected from the group consisting of HIV, Herpes simplex virus, Herpes zoster virus, Epstein-Barr virus, and Cytomegalovirus.

13. The method of claim 1, wherein the vertebrate is a bird or a mammal.

14. The method of claim 13, wherein the bird is selected from the group consisting of *Columba livia, Gallus domesticus,* and *Meleagris gallopavo.*

15. The method of claim 13, wherein the mammal is selected from the group consisting of *Primates, Carnivora, Proboscidea, Perissodactyla, Artiodactyla, Rodentia,* and *Lagomorpha.*

16. The method of claim 15, wherein the mammal is selected from the group consisting of *Canis familiaris, Felis catus, Elephas maximus, Equus caballus, Sus domesticus, Camelus dromedarius, Cervus axis, Giraffcamelopardalis, Bos taurus, Caprhircus, Ovis ries, Mus musculus, Lepus brachyurus, Mesocricetus auratus, Caviporcellus, Meriones unguiculatus,* and *Homo sapiens.*

17. The method of claim 16, wherein the mammal is a *Homo sapiens.*

18. The method of claim 1, wherein administering the antimicrobial peptide is one selected from the group consisting of conjunctivally, nasally, buccally, orally, rectally, vaginally, epidermally, and parenterally.

19. The method of claim 18, wherein administering is conjunctivally.

20. The method of claim 19, wherein the administering conjuctivally comprises administering at least one selected from the group consisting of an ophthalmic solution, an ophthalmic suspension, an ophthalmic gel, an ophthalmic ointment and an ophthalmic strip/insert.

21. The method of claim 1, wherein the antimicrobial peptide is administered before a cause of the ophthalmic infection is determined.

22. The method of claim 1, wherein the antimicrobial peptide is administered after a cause of the ophthalmic infection is determined.

23. The method of claim 1, wherein the effective ophthalmologically amount of the peptide is at least $10^{-13}$ Molar.

24. The method of claim 23, wherein the effective ophthalmologically amount of the peptide is at least $10^{-8}$ Molar.

25. A method of treating an ophthalmic infection comprising administering an ophthalmologically effective amount of an antimicrobial peptide to a *Homo sapiens,* wherein the *Homo sapiens* is inflicted with the ophthalmic infection, wherein the antimicrobial peptide is selected from the group consisting of KPV, MEHFRWG (SEQ ID NO: 1), HGRWGKPV (SEQ ID NO: 2), SYSMEHFRWGKPV (SEQ ID NO: 3), a KPV dimer, and a biologically functional equivalent thereof.

26. The method of claim 25, wherein the antimicrobial peptide is selected from the group consisting of KPV, MEHFRWG (SEQ ID NO:1), HFRWGKPV (SEQ ID NO:2), a KPV dimer, and SYSMEHFRWGKPV (SEQ ID NO:3).

27. The method of claim 25 or 26 wherein the KPV dimer is selected from the group consisting of VPK-Cys-s-s-Cys-KPV (SEQ ID NO:4), VPK-DCys-s-s-Cys-KPV, VPK-Pen-s-s-Cys-KPV (SEQ ID NO:6), VPK-Pen-s-s-DCys-KPV, VPK-DPen-s-s-Cys-KPV, VPK-DPen-s-s-D Cys-KPV, VPK-DPen-s-s-DPen-KPV, VPK-Pen-s-s-Pen-KPV (SEQ ID NO:7), VPK-hCys-s-s-Cys-KPV (SEQ ID NO:8), VPK-hCys-s-s-DCys-KPV, VPK-hCys-s-s-hCys-KPV (SEQ ID NO:9), VPK-DhCys-s-s-DhCys-KPV, VPK-DhCys-s-s-hCys-KPV, VPK-hCys-s-s-Pen-KPV (SEQ ID NO:10), VPK-hCys-s-s-DPen-KPV, and VPK-DhCys-s-s-DPen-KPV.

28. The method of claim 25, wherein the ophthalmic infection is selected from the group consisting of a bacterial ophthalmic infection, a fungal ophthalmic infection, and a viral ophthalmic infection.

29. The method of claim 28, wherein the ophthalmic infection is bacterial and comprises at least one selected from the group consisting of *Staphylococcus, Streptococcus, Treponema, Pneumococcus, Gonococcus, Haemophilus, Klebsiella, Neisseria, Chlamydia, Mycobacterium, Flavobacterium, Serratia, Propionibacterium,* an *Actinomyces, Pseudomonas, Corynebacterium, Meningococcus,* and an *Euterococcus.*

30. The method of claim 29, wherein the bacterial ophthalmic infection comprises *Staphylococcus* or *Streptococcus.*

31. The method of claim 30, wherein the bacterial ophthalmic infection comprises at least one selected from the group consisting of *Staphylococcus aureus, Staphylococcus epidermidis, Streptococcus viridans,* or *Streptococcus pneumoniae.*

32. The method of claim 28, wherein the ophthalmic infection is fungal and comprises at least one selected from the group consisting of *Microsporum, Trichophyton, Aspergillus, Leptothrix, Sporotrichum, Fusarium, Cephalosporium, Cyptococcus, Phycomycetes,* or *Candida.*

33. The method of claim 32, wherein the fungal ophthalmic infection comprises *Aspergillus* or *Candida.*

34. The method of claim 32, wherein the fungal ophthalmic infection comprises *Aspergillus fumigatus* or *Candida albicans.*

35. The method of claim 28, wherein the ophthalmic infection is viral and comprises at least one selected from the group consisting of Poxvirus, Herpesvirus, Adenovirus, Paramyxovirus or HIV.

36. The method of claim 35, wherein the viral ophthalmic infection comprises at least one selected from the group consisting of HIV, Herpes simplex virus, Herpes zoster virus, Epstein-Barr virus, or Cytomegalovirus.

37. The method of claim 25, wherein administering the antimicrobial peptide is one selected from the group consisting of conjunctivally, nasally, buccally, orally, rectally, vaginally, epidermally, and parenterally.

38. The method of claim 37, wherein administering is conjunctivally.

39. The method of claim 38, wherein administering conjuctivally comprises administering at least one selected from the group consisting of an ophthalmic solution, an ophthalmic suspension, an ophthalmic gel, an ophthalmic ointment or an ophthalmic strip/insert.

40. The method of claim 25, wherein the antimicrobial peptide is administered before a cause of the ophthalmic infection is determined.

41. The method of claim 25, wherein the antimicrobial peptide is administered after a cause of the ophthalmic infection is determined.

42. The method of claim 25, wherein the effective ophthalmologically amount of the peptide is at least $10^{-13}$ Molar.

43. The method of claim 42, wherein the effective ophthalmologically amount of the peptide is at least $10^{-8}$ Molar.

* * * * *

SEQUENCE LISTING

```
<160> NUMBER OF SEQ ID NOS: 11

<210> SEQ ID NO 1
<211> LENGTH: 7
<212> TYPE: PRT
<213> ORGANISM: Homo sapiens

<400> SEQUENCE: 1

Met Glu His Phe Arg Trp Gly
 1               5

<210> SEQ ID NO 2
<211> LENGTH: 8
<212> TYPE: PRT
<213> ORGANISM: Homo sapiens

<400> SEQUENCE: 2

His Phe Arg Trp Gly Lys Pro Val
 1               5

<210> SEQ ID NO 3
<211> LENGTH: 13
<212> TYPE: PRT
<213> ORGANISM: Homo sapiens

<400> SEQUENCE: 3

Ser Tyr Ser Met Glu His Phe Arg Trp Gly Lys Pro Val
 1               5                  10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (4)..(5)
<223> OTHER INFORMATION: Disulfide bond between residues 4 and 5

<400> SEQUENCE: 4

Val Pro Lys Cys Cys Lys Pro Val
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Lys Pro Val
 1

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)
<223> OTHER INFORMATION: Pen
<220> FEATURE:
<221> NAME/KEY: DISULFID
<222> LOCATION: (4)..(5)
<223> OTHER INFORMATION: Disulfide bond between residues 4 and 5

<400> SEQUENCE: 6

Val Pro Lys Xaa Cys Lys Pro Val
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Pen
<220> FEATURE:
<221> NAME/KEY: DISULFID
<222> LOCATION: (4)..(5)
<223> OTHER INFORMATION: Disulfide bond between residues 4 and 5

<400> SEQUENCE: 7

Val Pro Lys Xaa Xaa Lys Pro Val
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: hCys
<220> FEATURE:
<221> NAME/KEY: DISULFID
<222> LOCATION: (4)..(5)
<223> OTHER INFORMATION: Disulfide bond between residues 4 and 5

<400> SEQUENCE: 8

Val Pro Lys Cys Cys Lys Pro Val
 1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: hCys
<220> FEATURE:
<221> NAME/KEY: DISULFID
<222> LOCATION: (4)..(5)
<223> OTHER INFORMATION: Disulfide bond between residues 4 and 5

<400> SEQUENCE: 9

Val Pro Lys Cys Cys Lys Pro Val
 1               5
```

```
<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: hCys
<220> FEATURE:
<221> NAME/KEY: DISULFID
<222> LOCATION: (4)..(5)
<223> OTHER INFORMATION: Disulfide bond between residues 4 and 5
<220> FEATURE:
<221> NAME/KEY: MOD_RES
<222> LOCATION: (5)
<223> OTHER INFORMATION: Pen

<400> SEQUENCE: 10

Val Pro Lys Cys Xaa Lys Pro Val
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Ac-Cys
<220> FEATURE:
<221> NAME/KEY: DISULFID
<222> LOCATION: (4)..(5)
<223> OTHER INFORMATION: Disulfide bond between residues 4 and 5

<400> SEQUENCE: 11

Val Pro Lys Cys Cys Lys Pro Val
 1               5
```